(12) United States Patent
Ozaki

(10) Patent No.: US 6,468,041 B2
(45) Date of Patent: Oct. 22, 2002

(54) MAGNETICALLY LEVITATED APPARATUS

(75) Inventor: Takayoshi Ozaki, Iwata (JP)

(73) Assignee: NTN Corporation, Osaka (JP)

( * ) Notice: Subject to any disclaimer, the term of this patent is extended or adjusted under 35 U.S.C. 154(b) by 0 days.

(21) Appl. No.: 09/861,886

(22) Filed: May 22, 2001

(65) Prior Publication Data

US 2002/0012594 A1 Jan. 31, 2002

(30) Foreign Application Priority Data

May 25, 2000 (JP) ........................................ 2000-154769

(51) Int. Cl.[7] ................................................. F04B 49/00
(52) U.S. Cl. ..................... 417/44.1; 417/45; 417/410.1; 417/420; 417/423.4; 417/423.7; 417/423.12; 600/3; 600/16; 600/17; 600/151; 415/118; 415/203; 415/900
(58) Field of Search .................... 417/44.1, 45, 410.1, 417/420, 423.4, 423.7, 423.12; 415/203, 900; 600/3, 16, 151; 327/552, 556

(56) References Cited

U.S. PATENT DOCUMENTS 4,891,744 A * 1/1990 Yamamoto et al. ............ 363/89
5,911,558 A * 6/1999 Nakazeki et al. ............ 415/900
6,087,598 A * 7/2000 Munch ........................ 177/144
6,126,966 A * 10/2000 Nakazeki et al. .............. 600/17

FOREIGN PATENT DOCUMENTS

JP          2522168       * 10/1996

* cited by examiner

Primary Examiner—Charles G. Freay
Assistant Examiner—John F Belena
(74) Attorney, Agent, or Firm—McDermott, Will & Emery

(57) ABSTRACT

There is provided a magnetically levitated apparatus wherein an impeller has one side supported by an electromagnet and the other side supported and magnetically levitated by an attractive force created between a permanent magnet and a permanent magnet of a motor rotor rotated by a motor stator to rotate the impeller and a magnetic bearing sensor provides an output which is in turn rectified and thus shifted to have a gain adjusted and subsequently a notch filter removes a carrier wave frequency component used in the magnetic bearing sensor, to prevent a PID compensator from causing voltage saturation attributed to high frequency noise.

10 Claims, 6 Drawing Sheets

CROSS SECTION TAKEN ALONG IB-IB

MAGNETICALLY LEVITATED APPARATUS

BACKGROUND OF THE INVENTION

1. Field of the Invention

The present invention relates to magnetically levitated (maglev) apparatus and more specifically to those magnetically levitating an impeller to deliver liquid such as blood.

2. Description of the Background Art

FIG. 7 is a vertical cross section of a maglev liquid pump apparatus as one example of a conventional maglev apparatus and a block diagram of a controller thereof. In FIG. 7 a magnetically levitated liquid pump apparatus 100 is configured with an electromagnet unit 120, a pump unit 130 and a motor unit 140 housed in a cylindrical housing 101. Electromagnet unit 120 has an electromagnet 121 and a magnetic bearing sensor 122 incorporated therein. Housing 101 has on one side a side wall having a center provided with an inlet 102 introducing a liquid. At least three electromagnets 121 and at least three magnetic bearing sensors 122 surround inlet 102. Electromagnets 121 and magnetic bearing sensors 122 are attached to a partition 103 separating electromagnet unit 120 and pump unit 130 from each other.

In pump unit 130 an impeller 131 is rotatably housed and it has a portion closer to electromagnet unit 120, or closer to one side, that is supported by electromagnet 121 contactless through partition 103, and magnetic bearing sensor 122 senses the distance as measured from one side of impeller 131. Impeller 131 has the other side with a permanent magnet 132 buried therein. Motor unit 140 houses a motor 141 and a rotor 142. Rotor 142 has a surface facing pump unit 130 and having a permanent magnet 143 buried therein, opposite to permanent magnet 132 buried in impeller 131, with partition 104 disposed therebetween.

In the liquid pump apparatus thus configured, magnetic bearing sensor 122 provides an output which is in turn input to a sensor circuit 201 included in a controller 200 and sensor circuit 201 detects the distance between one side of impeller 131 and magnetic bearing sensor 122. Sensor circuit 201 provides an output which is in turn input to a PID compensator 202 to provide PID compensation and PID compensator 202 provides an output which is in turn amplified by a power amplifier 203 and thus applied to electromagnet 121 to control attractive force provided toward the opposite side of impeller 131.

Furthermore impeller 131 has a portion closer to motor unit 140 that is affected by the attractive force introduced by permanent magnets 132 and 143 and impeller 131 is magnetically levitated by a non-controlled bearing provided by permanent magnets 132 and 143 and a controlled bearing provided by electromagnet 121. A motor control circuit 205 provides a control signal which is in turn applied to a power amplifier 204. Power amplifier 204 drives motor 141 and the motor's driving force rotates impeller 131 and blood or any other similar liquid introduced through inlet 102 is output through an outlet (not shown) formed at pump unit 130.

The FIG. 7 magnetic bearing sensor 122 is a reluctance sensor using a carrier wave. This reluctance sensor is provided opposite to impeller 131 with the FIG. 7 partition 103 disposed therebetween. Note that partition 103 is formed of conductive material, particularly titanium for blood pumps owing to its compatibility with blood. The reluctance sensor generates a magnetic field, which introduces an eddy current in the conductive titanium and would thus impair the sensor's sensitivity.

In order to avoid this the carrier wave is adapted to have a low frequency range. This, however, may significantly affect controlling the magnetic bearing. More specifically, a reluctance sensor using a carrier wave provides a detection with a phase delay for down to a frequency approximately two decades lower than that of the carrier wave, e.g., 100 Hz for a carrier wave frequency of 10 kHz. To compensate for this to reliably control the magnetic bearing, PID compensator 202 needs to be constructed to lead a phase to a high frequency range. Consequently PID compensator 202 has a gain increased and a component of the carrier frequency contained in the sensor output causes voltage saturation in a circuit portion internal to PID compensator 202 and thus prevents reliable control.

SUMMARY OF THE INVENTION

Therefore the present invention mainly contemplates a magnetic bearing apparatus capable of removing a carrier wave frequency component used in a magnetic bearing sensor, to provide reliably control.

Generally the present invention provides a magnetically levitated apparatus including: a drive unit driving and thus levitating a body to be levitated; a magnetic position detection circuit using a carrier wave signal to detect a position of the body as the body levitates; a controlled magnetic bearing unit operative in response to an output of the magnetic position detection circuit to support the body without contacting the body; a control circuit operative in response to a signal output from the magnetic position detection circuit to control the controlled magnetic bearing unit, wherein between the magnetic position detection circuit and the body there exists a partition formed of a conductive material; and a filter connected between the magnetic position detection circuit and the control circuit to remove a carrier wave signal output from the magnetic position detection circuit.

Thus in the present invention a filter can remove a carrier wave frequency component from a sensor output before amplification. Thus voltage saturation in the control circuit can be prevented to provide reliable control.

More preferably the magnetic position detection circuit includes: a reluctance sensor provided adjacent to the body and having an inductance varying as the distance between the reluctance sensor and the body varies; and a sensor circuit operative in response to an output of the reluctance sensor to output a signal varying as the inductance varies.

Furthermore the present apparatus further includes a carrier wave generation circuit feeding the magnetic position detection circuit with a carrier wave signal, wherein: the sensor circuit outputs the carrier wave signal with the amplitude varying as the spacing between the magnetic position detection circuit and the body varies; and the filter removes a center frequency of the carrier wave signal.

Furthermore the filter is a band eliminating filter arranged immediately subsequent to the sensor circuit.

Furthermore, the drive unit includes a non-controlled magnetic bearing unit magnetically coupled with the body at one side and a drive unit operative to rotate the body via the magnetic bearing unit, and the controlled magnetic bearing unit is magnetically coupled with the body at the other side.

Furthermore the body is an impeller rotated to output a liquid and the magnetically levitated apparatus configures a magnetically levitated pump.

The magnetically levitated apparatus further includes a drive unit rotatably driving the impeller through magnetic-coupling.

Furthermore the impeller is rotated to output blood and the magnetically levitated apparatus configures a blood pump apparatus.

Furthermore the impeller is rotated to output blood and the magnetically levitated apparatus configures a blood pump apparatus.

More preferably the body is rotated to rotate a vane and the magnetically levitated apparatus configures a turbo molecular pump.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1A:
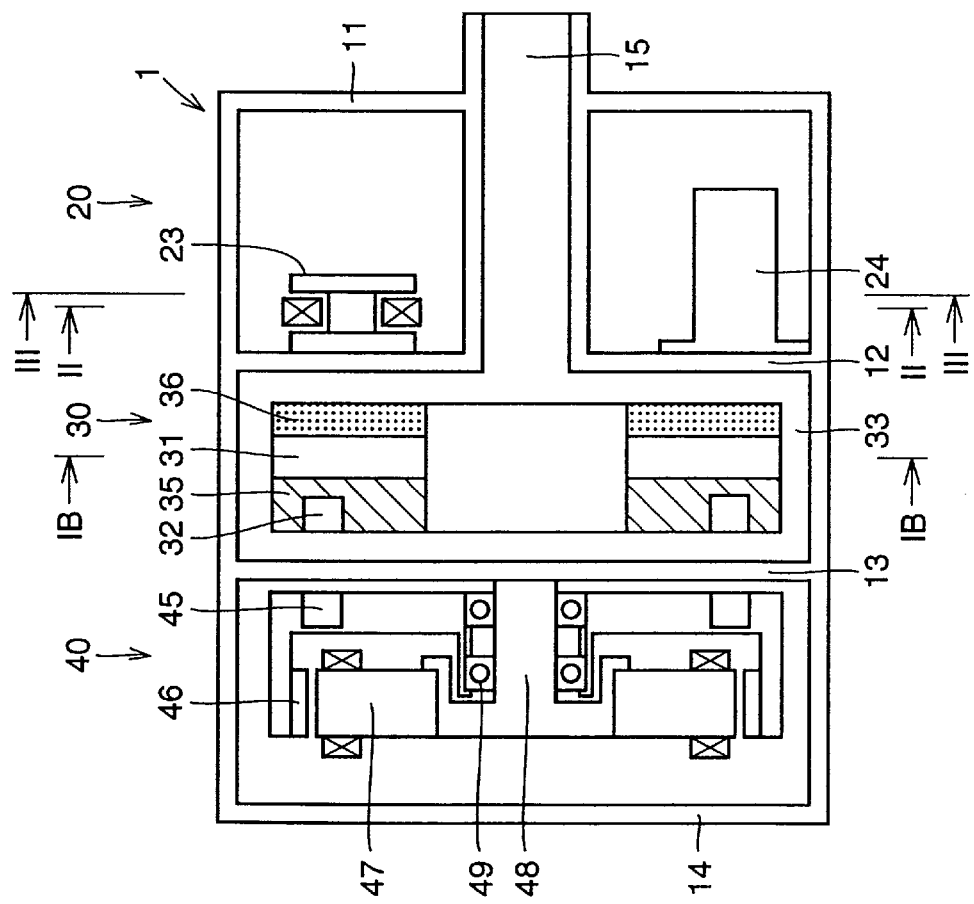
FIGS. 1A and 1B show a first embodiment of the present invention.
Figure 1B:
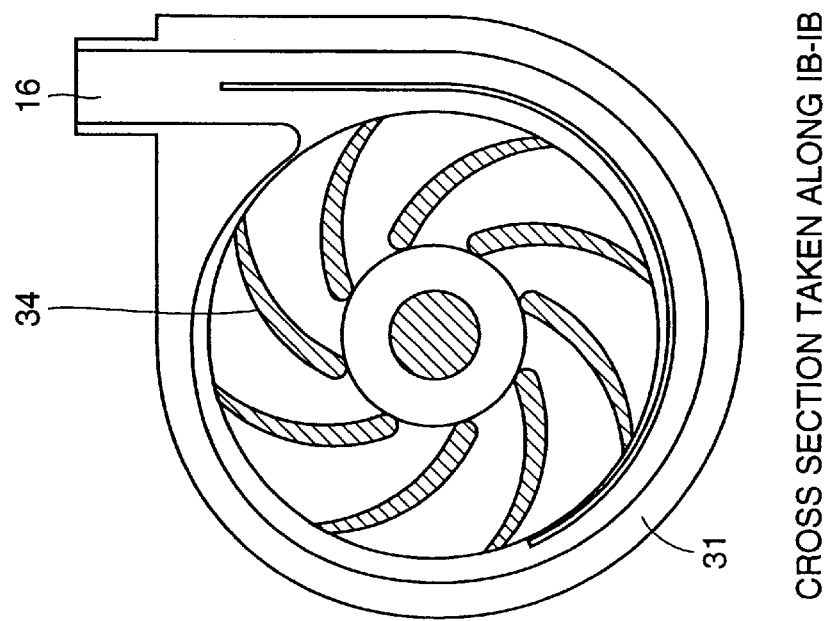
Figure 2:
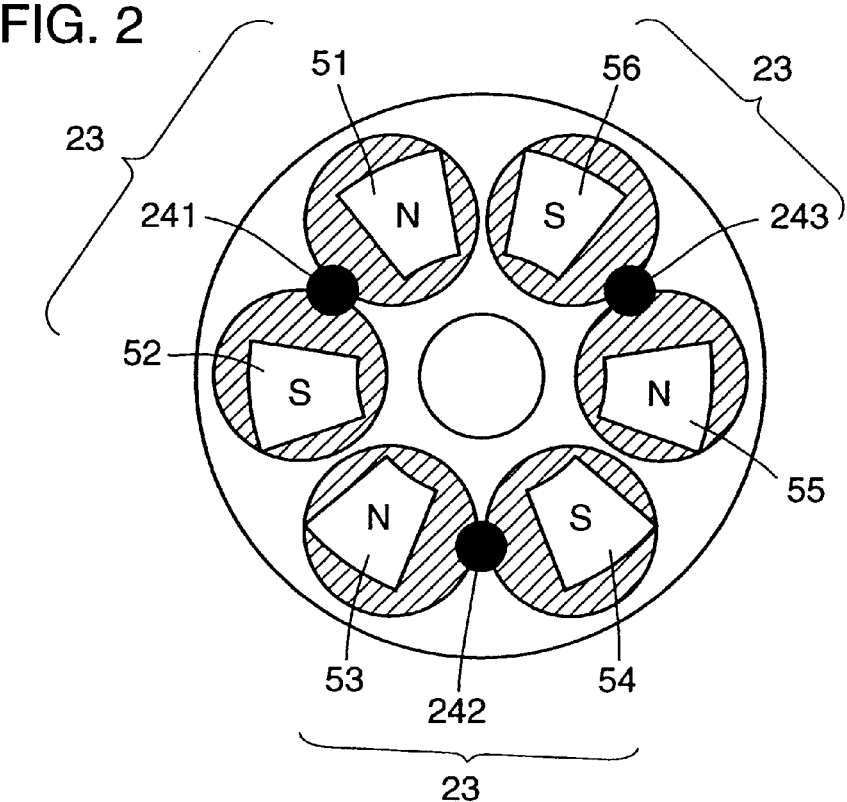
FIG. 2 is a cross section taken along line II—II of FIG. 1A.
Figure 3:
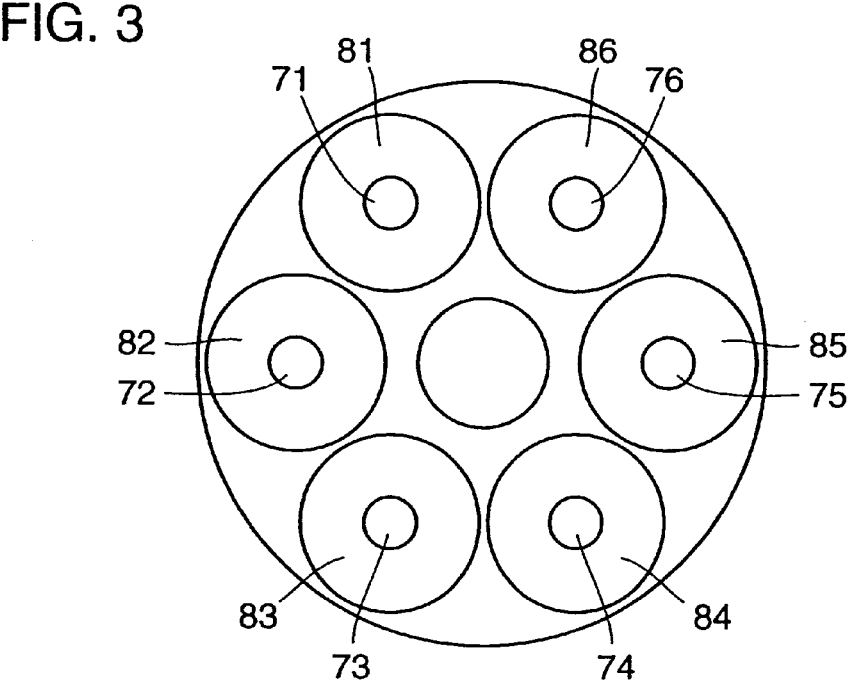
FIG. 3 is a cross section taken along line III—III of FIG. 11A.

FIGS. 1A and 1B show a magnetically levitated liquid pump apparatus in one embodiment of the present invention. More specifically, FIG. 1A is a vertical cross section thereof and FIG. 1B is a cross section thereof taken along line IB—IB of FIG. 1A. FIG. 2 is a cross section taken along line II—II of FIG. 1A and FIG. 3 is a cross section taken along line III—III of FIG. 1A. FIG. 2 shows a sensor unit in a simple manner and FIG. 3 omits the sensor unit.

With reference to FIGS. 1A and 1B, the liquid pump apparatus includes a cylindrical casing 1 axially separated by partitions 11, 12, 13 and 14 to have sections housing a magnetic bearing unit 20, a pump unit 30 and a motor unit 40, respectively. Casing 1 is formed for example of plastic, ceramic, metal or the like, although of casing 1, partition 12 provided between magnetic bearing unit 20 and pump unit 30 and partition 13 provided between pump unit 30 and motor unit 40 are not allowed to be formed of magnetic material and they are accordingly formed of non-magnetic material.

At pump unit 30 casing 1 is internally provided with a pump chamber 33 in which an impeller 31 rotates to output through an outlet 16 shown in FIG. 1B a fluid introduced through an inlet 15. Impeller 31 has a plurality of vanes 34 spirally provided, as shown in FIG. 1B. Impeller 31 includes a non-magnetic member 35 having a permanent magnet 32 configuring a non-controlled magnetic bearing and a soft magnetic member 36 corresponding to a rotor of a controlled magnetic bearing. Permanent magnet 32 is divided in a circumferential direction of impeller 31 and adjacent magnets are magnetized to have opposite magnetic poles.

Note that by coating the entire interior of pump chamber 33 with heparin serving as an anticoagulant, formation of thrombus can be prevented therein and the liquid pump apparatus can thus be used as a blood delivering pump. In this example, the heparin coating can effectively limit activation of coagulation system, protect platelets, limit activation, activation of inflammation system, activation of fibrinolysis system, contagion, and the like.

In FIG. 1A, the dotted portion of impeller 31 is formed of soft magnetic material 36 and the remainder thereof is shown formed of nonmagnetic material. If the pump is used to deliver a corrosive fluid such as blood, the soft magnetic material is preferably a highly corrosive-resistant, ferritic stainless steel (SUS447J, SUS444 or the like) and the non-magnetic material is preferably a highly corrosive-resistant, austenitic stainless steel (SUS316L or the like) or titanium alloy, pure titanium or the like.

Opposite to a side of impeller 31 having permanent magnet 32, a cylindrical member 48 is provided in motor unit 40, extending from a center of partition 13 toward partition 14. Cylindrical member 48 has an external peripheral surface provided with a motor bearing 49 provided in the form of a ball or roller bearing which supports a motor rotor 46 rotatably. Cylindrical member 48 has an end with a motor stator 47 attached thereto. Motor rotor 46 is driven by motor stator 47 to rotate. Motor rotator 46 is provided with the same number of permanent magnets 45 as permanent magnets 32 of impeller 31 opposite thereto to provide attractive force. Adjacent permanent magnets 45 are magnetized to have opposite magnetic poles.

Note that while the motor is a synchronous motor including a DC brushless motor, a non-synchronous motor including an induction motor, or the like, it may be any kind of motor.

Provided in electromagnet unit 20 are an electromagnet 23 and a magnetic bearing sensor 24, attached on a wall of partition 12 provided between electromagnet unit 20 and pump unit 30, opposite to that side of impeller 31 having soft magnetic member 36. Electromagnet 23 and magnetic bearing sensor 24 allow impeller 31 to be held at the center of pump chamber 33, matching the attractive force produced between permanent magnets 32 and 45.

Thus the heat generated at electromagnet 23 can be transferred to partition 12 and thus cooled by a liquid existing in pump unit 30. Similarly, the heat generated at motor stator 47 can also be transferred through cylindrical member 48 to partition 13 and thus cooled by the liquid existing in motor unit 30. This can reduce heat transfer to outside casing 1 and also reduce heat transfer to magnetic bearing sensor 24 to provide a reliable sensing operation. Furthermore, if partitions 12 and 13 are increased in thickness to have a level of strength allowing electromagnet 23, magnetic bearing sensor 24 and motor stator 47 to be attached thereto, housing 1 can advantageously have an outer-diameter portion reduced in thickness.

Electromagnet 23 and magnetic bearing sensor 24 are arranged, as shown in FIGS. 2 and 3. More specifically, paired electromagnets 23 have magnetic poles 51 and 52 with a sensor 241 arranged therebetween, magnetic poles 53 and 54 with a sensor 242 arranged therebetween, and magnetic poles 55 and 56 with a sensor 243 arranged therebetween. Sensors 241 to 243 are typically a magnetic sensor, such as a reluctance sensor.

Furthermore, as shown in FIG. 3, electromagnets 23 have their respective yokes 71–76 in the form of a column with electromagnet coils 81–86 wound therearound, respectively.

Circumferentially arranging magnetic poles 51-56 can increase the space housing electromagnet coils 81–86 that can be housed in electromagnet unit 20. This ensures a large space for winding the coils without increasing the size of the pump. Increasing a space for housing a coil in turn allows an electromagnet coil to have an increased turn count and an increased wire diameter and can thus decrease the power consumption of the electromagnet.

Furthermore, electromagnet yokes 71–76 in the form of a column can facilitate winding electromagnet coils 81–86 around electromagnet yokes 71–76, respectively. Electromagnet yokes 71–76 having a simple geometry also ensure insulation from electromagnet coils 81–86. While electromagnet yokes 71–76 are cylindrical, they may be in the form of a prism, which can facilitate winding coils and thus ensuring a withstand voltage between the coils and the yokes.

Furthermore while in FIGS. 2 and 3 electromagnet yokes 71–76 and electromagnet coils 81-86 are all arranged in a single circle, they may not thus be arranged if required to effectively ensure a space for housing the same.

With the magnetic bearing having each electromagnet with its magnetic pole and yoke arranged circumferentially, the magnetic bearing unit is not required to have a large space and the electromagnet yoke can be provided in a cylinder or a prism.

Figure 4:
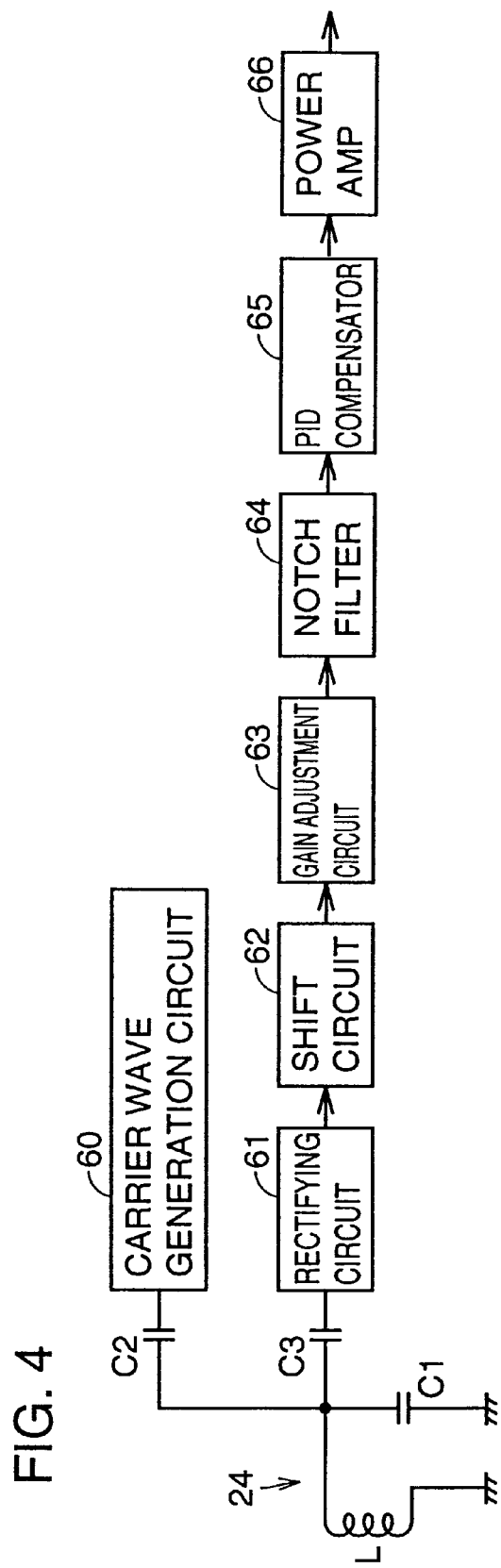
FIG. 4 is a schematic block diagram showing a controller controlling a magnetically levitating apparatus of the present invention.

FIG. 4 is a block diagram showing an example of a controller controlling a liquid pump as a magnetically levitated apparatus in the first embodiment of the present invention.

In FIG. 4, the FIG. 1A magnetic bearing sensor 24 has an inductance L and receives a carrier wave signal for example of 100 kHz from a carrier wave generation circuit 60 via a capacitor C2. Magnetic bearing sensor 24 outputs via a capacitor C3 to a rectifying circuit 61 a detection signal with the carrier wave having an amplitude varying as the spacing between sensor 24 and the FIG. 1A impeller 31 varies. Rectifying circuit 61 rectifies the detection signal to provide a dc signal which is in turn output via a shift circuit 62 to a gain adjustment circuit 63.

Shift circuit 62 and gain adjustment circuit 63 adjust the sensor output's zero point and gain and the resultant sensor signal is fed to a notch filter 64 to have the carrier wave's center frequency component removed.

Figure 5:
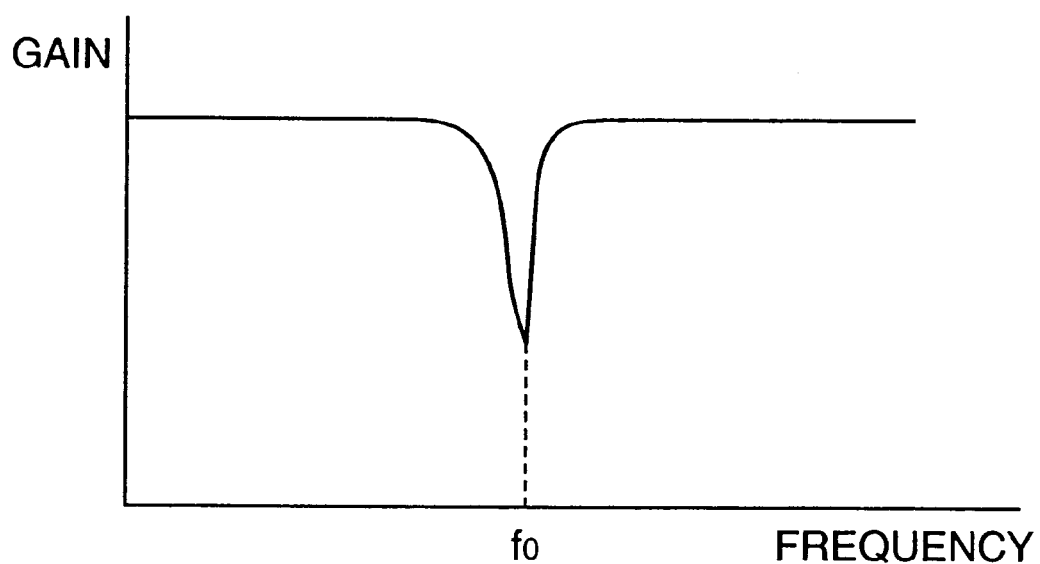
FIG. 5 represents a frequency cut-off characteristic of a notch filter shown in FIG. 4.

FIG. 5 represents a frequency cut-off characteristic of the FIG. 4 notch filter 64. As shown in FIG. 5, notch filter 64 is a band elimination filter abruptly attenuating a center frequency fo of a carrier wave and it can thus remove a component of a carrier wave frequency from a component of a sensor output. Consequently if a PID compensator 65, which is connected at a subsequent stage, is increased in gain a circuit portion internal thereto would not have voltage saturation and reliable control can thus be provided. PID compensator 65 provides an output which is in turn input to a power amplifier 66 to drive electromagnet 23.

Note that while notch filter 64 is connected at a stage immediately preceding PID compensator 65 it may alternatively be connected closer to the output of magnetic bearing sensor 24.

Figure 6:
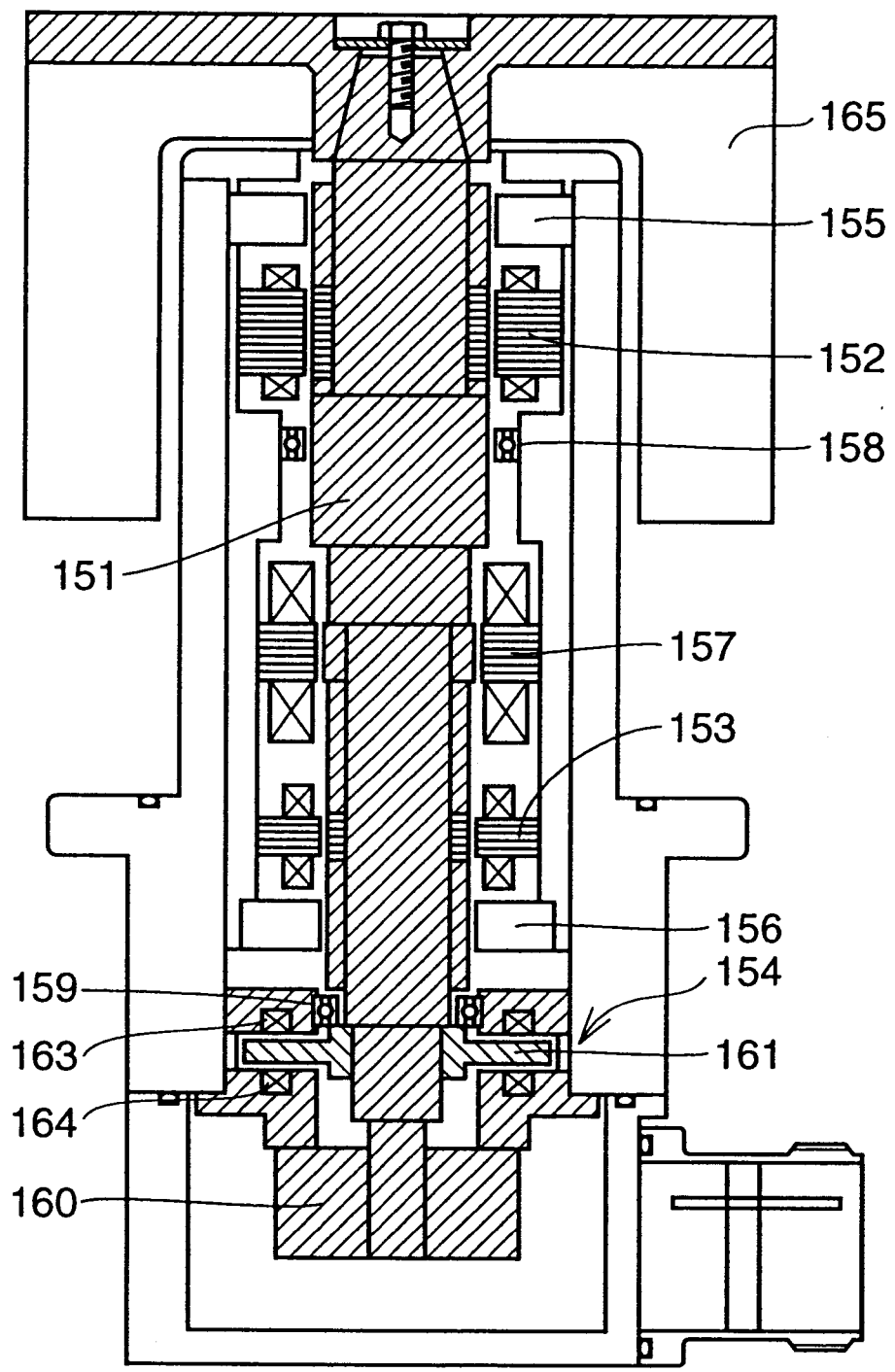
FIG. 6 is a cross section of a spindle for a turbo molecular pump in a second embodiment of the present invention.
Figure 7:
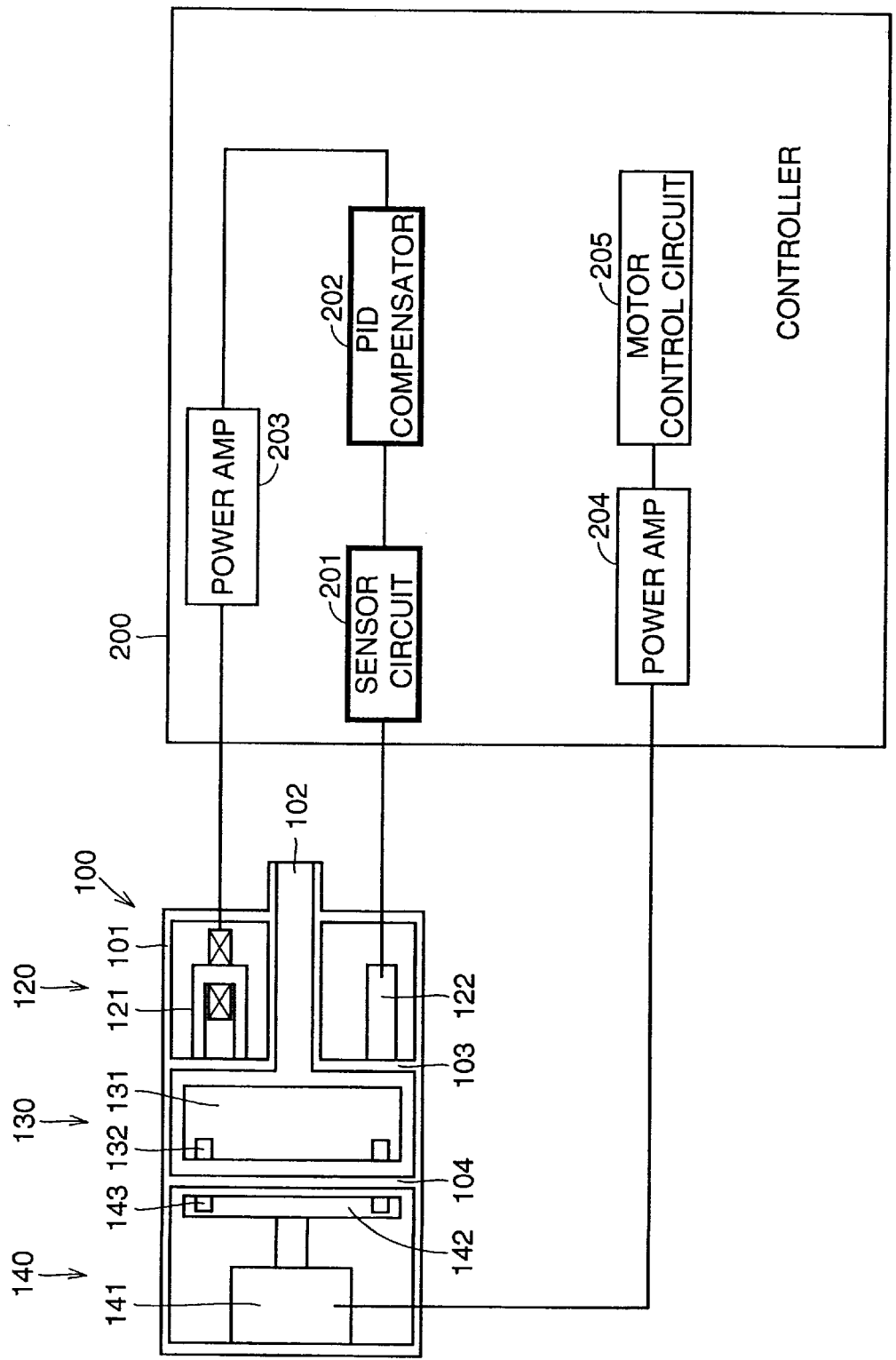
FIG. 7 is a vertical cross section of a conventional magnetically levitated liquid pump apparatus and a block diagram of a controller.

FIG. 6 is a cross section of a spindle for a turbo molecular pump as a magnetically levitated apparatus in a second embodiment of the present invention. In FIG. 6 a rotation shaft 151 has a radial direction supported by radial magnetic bearings 152, 153 configured of vertically arranged electromagnets and a thrust direction supported by a thrust magnetic bearing 154. Thrust bearing 154 is configured of a disk 161 fixed on a lower side of rotation shaft 151 and permanent magnets 163, 164 vertically sandwiching the disk. Radial magnetic bearings 152, 153 are vertically sandwiched by radial position sensors 155, 156 provided in the form of a magnetic sensor corresponding to a reluctance sensor and sensing a gap as measured from rotation shaft 151. Rotation shaft 151 has an upper portion with a vane 165 attached thereto to rotate to serve as a vacuum pump.

Between radial magnetic bearings 152 and 153 there is provided a motor 157 to rotatably drive rotation shaft 151. Below radial magnetic bearing 152 and radial position sensor 156 are arranged protecting ball or roller bearings 158, 159 supporting rotation shaft 151 for example when power supply is cut and rotation shaft 151 is thus not supported by radial magnetic bearings 152, 153. Rotation shaft 151 has a lower portion provided with a thrust position sensor 160 sensing a thrust position of rotation shaft 151. Thrust position sensor 160 is also provided in the form of a magnetic sensor corresponding to a reluctance sensor.

Such a turbo molecular pomp spindle thus configured has a disadvantage similar to that as has been described with reference to the conventional example as radial position sensors 155, 156 and thrust position sensor 160 are all reluctance sensors.

Accordingly if the FIG. 4 controller is arranged for each sensor and radial position sensors 155 and 156 and thrust position sensor 160 each have an output connected to a notch filter provided at a stage preceding a PID compensator a carrier wave frequency component can be removed and if the notch filter's output is used to control the corresponding radial magnetic bearings 152, 153 and thrust magnetic bearing 153 reliable control can be provided.

Thus in an embodiment of the present invention a filter removing a carrier wave can be connected between magnetic position detection means and a control unit controlling a magnetic bearing unit. This can prevent a circuit connected at a stage subsequent to the filter from causing a voltage saturation attributed to a carrier wave component used by a sensor circuit. Thus reliable control can be provided.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A magnetically levitated apparatus comprising:
    a body to be levitated;
    a drive unit driving and thus levitating said body;
    a magnetic position detection circuit operative in response to a carrier wave signal to detect a position of said body as said body levitates;
    a controlled magnetic bearing unit operative in response to an output of said magnetic position detection circuit to support said body without contacting said body;
    a control circuit operative in response to a signal output from said magnetic position detection circuit to control said controlled magnetic bearing unit,
    wherein between said magnetic position detection circuit and said body there exists a partition formed of a conductive material; and
    a filter connected between said magnetic position detection circuit and said control circuit to remove a component of carrier wave frequency contained in a signal output from said magnetic position detection circuit.

2. The magnetically levitated apparatus of claim 1, wherein said magnetic position detection circuit includes:

a reluctance sensor provided adjacent to said body and having an inductance varying as a distance between said reluctance sensor and said body varies; and a sensor circuit operative in response to an output of said reluctance sensor to output a signal with an amplitude of said carrier wave signal varying as said inductance varies.

3. The magnetically levitated apparatus of claim 2, further comprising a carrier wave generation circuit feeding said magnetic position detection circuit with a carrier wave signal, wherein:

said sensor circuit outputs said carrier wave signal with said amplitude varying as a distance between said magnetic position detection circuit and said body varies; and said filter removes a frequency of said carrier wave.

4. The magnetically levitated apparatus of claim 3, wherein said filter is a band eliminating filter arranged immediately subsequent to said sensor circuit.

5. The magnetically levitated apparatus of claim 1, wherein said drive unit includes a non-controlled magnetic bearing unit magnetically coupled with said body at one side and a drive unit operative to rotate said body via said magnetic bearing unit, and said controlled magnetic bearing unit is magnetically coupled with said body at the other side.

6. The magnetically levitated apparatus of claim 1, said body being an impeller rotated to output a liquid, said magnetically levitated apparatus configuring a magnetically levitated pump.

7. The magnetically levitated apparatus of claim 5, further comprising a drive unit rotatably driving said impeller through magnetic-coupling.

8. The magnetically levitated apparatus of claim 6, said impeller being rotated to output blood, said magnetically levitated apparatus configuring a blood pump apparatus.

9. The magnetically levitated apparatus of claim 7, said impeller being rotated to output blood, said magnetically levitated apparatus configuring a blood pump apparatus.

10. The magnetically levitated apparatus of claim 1, said body being rotated to rotate a vane, said magnetically levitated apparatus configuring a turbo molecular pump.

* * * * *